United States Patent [19]

Lolachi

[11] 4,113,173
[45] Sep. 12, 1978

[54] CENTRIFUGAL LIQUID PROCESSING APPARATUS

[75] Inventor: Houshang Lolachi, Rockville, Md.

[73] Assignee: Baxter Travenol Laboratories, Inc., Deerfield, Ill.

[21] Appl. No.: 657,187

[22] Filed: Feb. 11, 1976

Related U.S. Application Data

[63] Continuation-in-part of Ser. No. 562,748, Mar. 27, 1975, abandoned.

[51] Int. Cl.² ............................ B04B 5/02; B04B 9/00
[52] U.S. Cl. ........................................ 233/25; 233/26
[58] Field of Search ............... 233/14 R, 14 A, 1 R, 233/1 D, 16, 14 B, 14 A, 23 R, 23 A, 24, 25, 7, 26, 27; 210/31 C, 198 C, DIG. 24; 23/259; 64/2 R; 74/217, 797

[56] References Cited

U.S. PATENT DOCUMENTS

| | | | |
|---|---|---|---|
| 2,559,299 | 7/1951 | Helling | 74/217 C |
| 3,115,794 | 12/1963 | Morin | 74/797 |
| 3,498,533 | 3/1970 | Schomburg | 233/7 |
| 3,586,413 | 6/1971 | Adams | 233/25 UX |
| 3,775,309 | 11/1973 | Ito et al. | 233/25 UX |
| 3,842,685 | 10/1974 | Philpott | 74/217 C |
| 3,885,735 | 5/1975 | Westberg | 233/25 |
| 3,994,805 | 11/1976 | Ito | 210/31 C |

OTHER PUBLICATIONS

*Science,* Sep. 1975, vol. 189, No. 4207, New Flow-Through Centrifuge without Rotating Seals Applied to Plasmapheresis, by Ito, Y. et al.

*Primary Examiner*—George H. Krizmanich
*Attorney, Agent, or Firm*—Henry W. Collins; George H. Gerstman; Eugene M. Cummings

[57] ABSTRACT

A centrifugal cell processing apparatus wherein a rotor assembly having a pair of containers for receiving a fluid to be processed by centrifugation is rotatably mounted on a rotor drive assembly, which is rotatably mounted on a stationary base. Liquid communication is maintained with the containers during rotation of the rotor by means of a flexible umbilical cable which extends from the containers to a location external to the apparatus by way of a passageway provided in the support shaft of the rotor assembly and a guide sleeve carried on and rotatably mounted to the rotor drive assembly. The rotor assembly is rotatably driven in the same direction as the rotor drive assembly with a speed ratio of 2:1 to prevent the umbilical cable from becoming completely twisted during operation of the apparatus. A guide sleeve may be provided on the rotor drive assembly to assist in installing the umbilical cable and to support the cable during operation.

8 Claims, 15 Drawing Figures

CENTRIFUGAL LIQUID PROCESSING APPARATUS

This application is a continuation-in-part of application Ser. No. 562,748, filed Mar. 27, 1975, and now abandoned.

BACKGROUND OF THE INVENTION

The present invention is directed generally to a fluid processing system, and more particularly to a centrifugal biological cell processing system and apparatus for processing or reconstituting blood and other biological cells wherein fluid communication is continuously maintained with rotating wash bags without the use of rotating seals or other rotating coupling elements, thereby maintaining the system sealed and free from contamination.

In recent years long term storage of human blood has been accomplished by separating out the plasma component of the blood and freezing the remaining red blood cell component in a liquid medium such as glycerol. Prior to use the glycerolized red blood cells are thawed and pumped into a centrifugating wash chamber where, while being held in place by centrifugation, they are washed with a saline solution which displaces the glycerol preservative. The resulting reconstituted blood is then removed from the wash chamber and packaged for use.

The aforedescribed blood conditioning process necessitates the transfer of glycerolized cell and saline wash solutions into the wash chamber, and the transfer of glycerol waste and reconstituted blood from the wash chamber, while the chamber is in motion. To avoid contamination of the blood or the exposure of persons involved in the processing operation to infection, these fluid transfer operations must be carried out within a sealed pre-sterilized flow system, preferably formed of a flexible plastic or similar material which can be disposed of after each use.

One drawback present in many such flow systems has been their use of a rotating seal or coupling element between that portion of the system carried by the centrifuge rotor and that portion of the system which remains stationary. While such rotating seals have provided generally satisfactory performance, they have been expensive to manufacture and have unnecessarily added to the cost of the flow systems. Furthermore, such rotating seals do introduce an additional component into the system which if defective can cause contamination of the blood being processed. This is particularly true when two different batches of blood are being simultaneously processed since the components of one blood batch must pass side-by-side through the rotating seal with the components of another blood batch. Also, such rotating seals by reason of inherent surface wear may introduce undesirable particulate matter into the fluid being processed.

Previous attempts at overcoming the problem of a rotating seal include the use of rotating carriages on which housings were rotatably mounted. Fluid communication was established with the housings by means of umbilical cables extending to the housings and planetary motion was imparted to the housings to prevent the cables from twisting. In one such system the housing and umbilical cable were permanently sealed together, and in another such system an inner liquid processing chamber was rotatably mounted within the housing and connected to the umbilical cable by a rotating seal. Unfortunately, in the former system the liquid being processed was subjected to conflicting radial and longitudinal accelerations, necessitating the provision of capillary passageways in the chamber and thus making the system unpractable for volume processing operations. In the latter system the expensive and trouble-prone rotating seal was still present. Furthermore, neither of these systems allowed the use of more than one liquid processing chamber, preventing the simultaneous processing of multiple batches of fluids.

Thus, the need exists for a centrifugal fluid processing system and apparatus wherein multiple batches of fluid can be simultaneously and efficiently processed without the use of capillary processing chambers, or rotating coupling elements between the centrifugating processing chambers and the stationary portions of the system. In apparatus described in U.S. Pat. No. 3,586,413 to Dale A. Adams energy transfer is accomplished between fixed and rotating elements by means of a flexible umbilical cable. The present invention encompasses the application of the principle of operation of the Adam's apparatus to the centrifugation of fluids, and particularly to the centrifugation of biological fluids such as blood, and improvements in such apparatus for this purpose.

SUMMARY OF THE INVENTION

The invention is directed to a centrifugal fluid processing system comprising a stationary base, a rotor drive assembly rotatably mounted to the base for rotation along a predetermined axis, and a rotor assembly including a least one fluid processing chamber, the rotor assembly being rotatably mounted with respect to the base for rotation along the axis. Means including a flexible umbilical cable segment are included for establishing fluid communication with the processing container, one end of the cable segment being fixed with respect to the base along the axis at one side of the rotor assembly, the other end of the cable segment being attached on the axis in rotationally locked engagement to the other side of the rotor assembly. Guide means are included for causing the umbilical cable segment to orbit about the axis with the motor drive assembly, and drive means are included for rotating the rotor assembly and the rotor drive assembly in the same direction with a speed ratio of 2:1 to prevent the umbilical cable from becoming completely twisted during operation of the apparatus.

The invention is further directed to a centrifugal fluid processing apparatus for use in conjunction with a flow system including at least one fluid processing chamber and a flexible umbilical cable segment having a plurality of integral passageways for establishing fluid communication with the processing chamber. The apparatus comprises a stationary base, a rotor drive assembly rotatably mounted to the base for rotation along a predetermined axis, a rotor assembly including means for receiving the processing chamber, the rotor assembly being rotatably mounted with respect to the base for rotation along the axis, and means including a stationary support member for anchoring one end of the cable at one side of the rotor assembly at a fixed position along the axis with respect to the base, the other end of the cable segment extending to the other side of the rotor assembly and being rotatably locked thereto along the axis. Guide means are provided for causing the umbilical cable to orbit about the axis with the rotor drive assembly, and drive means are provided for rotating the rotor drive assembly and the rotor drive assembly in the same direction about the axis with a speed ratio of 2:1 to prevent the umbilical cable from becoming completely twisted during operation of the apparatus.

The invention is further directed to a centrifugal apparatus for use in conjunction with a flexible communication conduit for maintaining communication with terminal means under centrifugation. The apparatus comprises a stationary base, a rotor drive assembly rotatably mounted to the base for rotation along a predetermined axis, and a rotor assembly including terminal means on one side thereof, the rotor assembly being rotatably mounted to the rotor drive assembly for rotation with respect thereto along the axis by means including a support shaft journaled to the drive assembly, the support shaft extending from the opposite side of the rotor assembly and including a central axially-extending aperture. Support means are provided for supporting the communication conduit above the one side of the rotor assembly along the axis. Guide means including a guide member on the rotor drive assembly are provided for guiding the communication conduit from the support means through the axially-extending aperture to the terminal, the guide means rotatably coupling the communication conduit to the rotor drive assembly with respect to the axis, and drive means are provided for rotating the rotor assembly and the rotor drive assembly in like directions with a speed ratio of 2:1 to maintain communication without twisting the conduit.

BRIEF DESCRIPTION OF THE DRAWINGS

The features of the present invention, which are believed to be novel, are set forth with particularity in the appended claims. The invention, together with the further objects and advantages thereof, may best be understood by reference to the following description taken in connection with the accompanying drawings, in the several figures of which like reference numerals identify like elements, and in which:

DESCRIPTION OF THE PREFERRED EMBODIMENT

Figure 1:
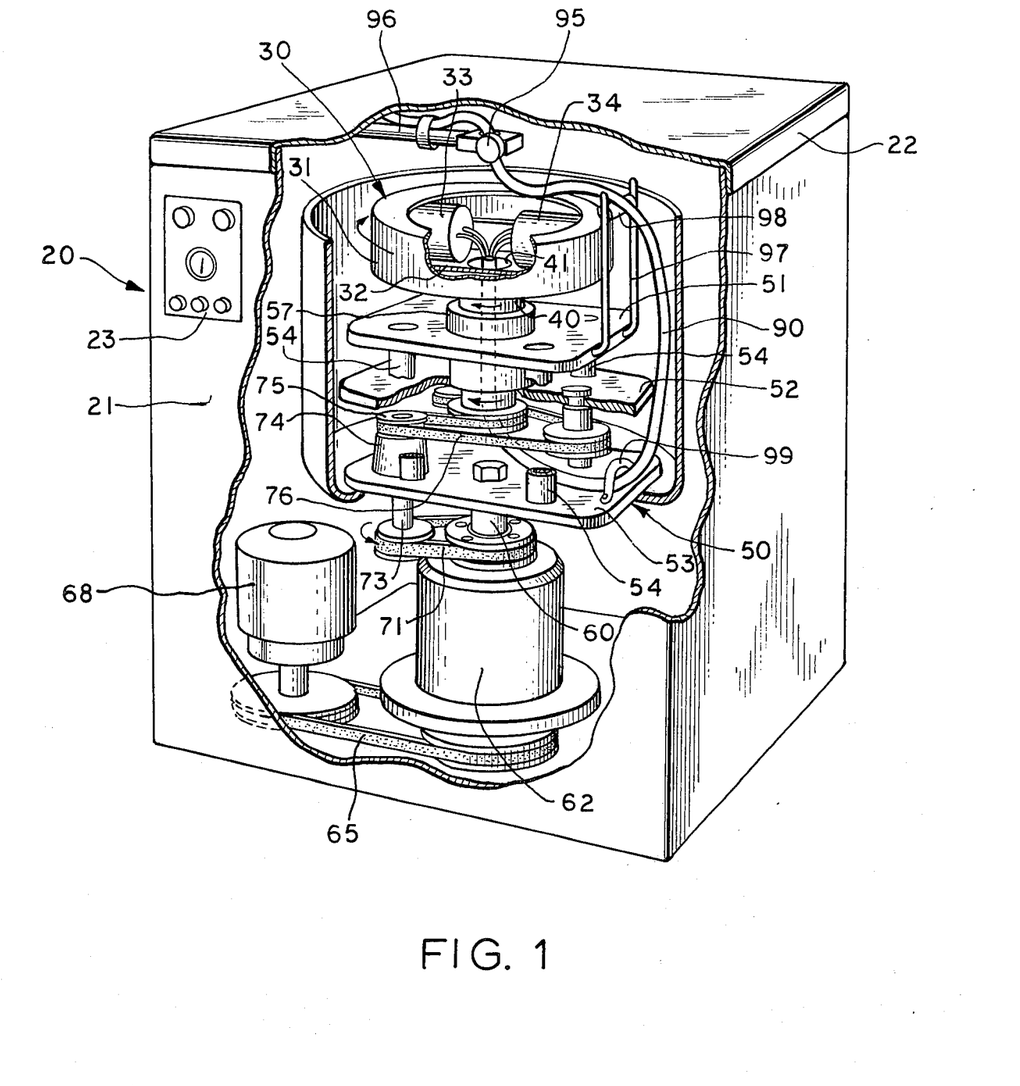
FIG. 1 is a perspective view of a centrifugal cell processing apparatus constructed in accordance with the invention partially broken away to show its rotor and rotor drive assemblies, cell wash bags, and umbilical cable for establishing fluid communication with the wash bags.
Figure 2:
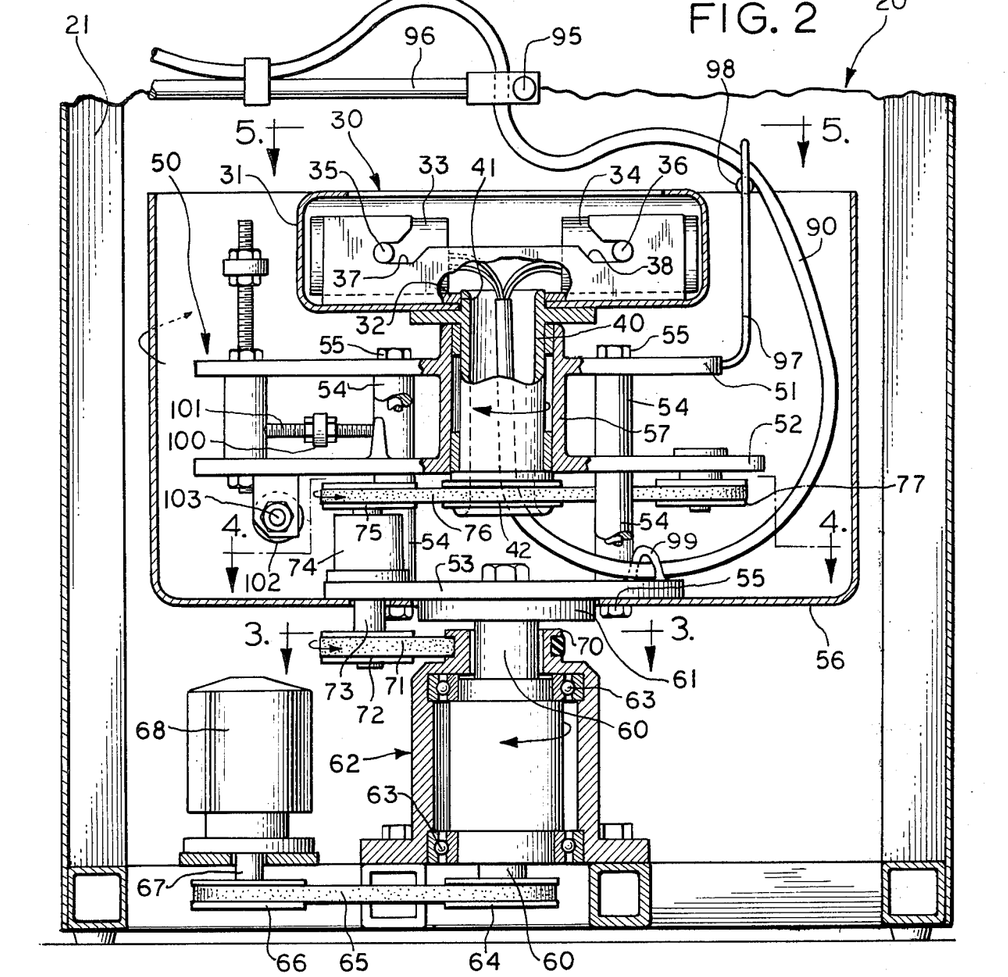
FIG. 2 is a front elevational view of the cell processing apparatus partially in cross section and partially broken away to show the details of the rotor and rotor drive assemblies.

Referring to the Figures, and particularly to FIGS. 1 and 2, a fluid processing system constructed in accordance with the invention is shown in the form of a centrifugal cell processing apparatus 20 wherein blood cells or the like to be processed are held in suspension in rotating wash bags by centrifugal force while being subjected to a counterflow of wash solution. The cell processing apparatus includes a cabinet or housing 21 which may be suitably insulated and lined to permit refrigeration of its interior. A hinged cover 22 provides access to the interior and a control panel 23 facilitates operator control of the operation of the apparatus.

The cell masses to be processed are subjected to centrifugal force by means of a rotor assembly 30 which includes a bowl-shaped wind shield 31 for reducing wind friction, a central support bracket 32, and a pair of cylindrical support cups 33 and 34 in which the wash bags are contained. Cups 33 and 34, which are preferably machined of aluminum or stainless steel, are mounted in diametrically opposed positions on bracket 32 by means of opposed pair of integral outwardly-projecting pins 35 and 36 which engage respective ones of complementarily dimensioned slots 37 and 38 in bracket 32.

Figure 10:
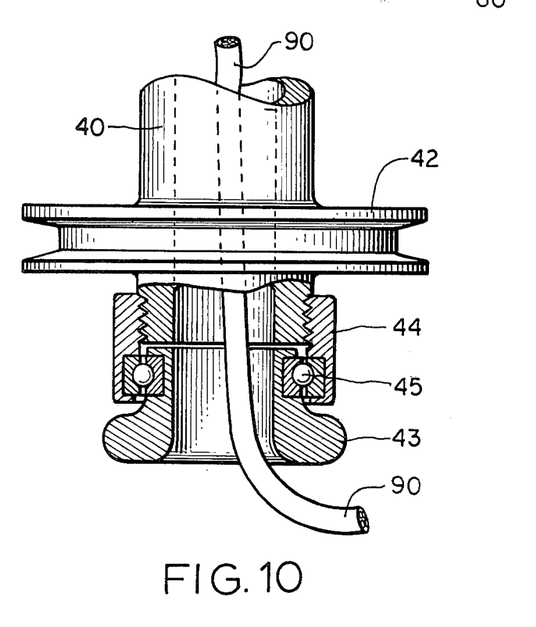
FIG. 10 is an enlarged front elevational view, partially in section, of the lead fairing utilized in the centrifugal liquid processing apparatus.

Bracket 32 is attached at its center to the flanged upper end of a hollow vertically-aligned rotor drive shaft 40, and includes a central aperture 41 for receiving the portion of the drive shaft which projects beyond the flange. The bottom end of drive shaft 40 is fitted with a rotor drive pulley 42 and a free-rotating fairing 43. As shown in FIG. 10, fairing 43 is held in position by means of a collar assembly 44 threaded onto the outside surface of the shaft, the collar assembly achieving a rotational engagement with fairing 43 by means of a plurality of ball bearings 45.

The cell processing apparatus 20 further includes a rotor drive assembly 50 which includes three horizontal plate-like members 51, 52 and 53 held in a unitary parallel-spaced configuration by a plurality of vertical spacers 54 and bolts 55, and a bowl-shaped wind shield 56, which is attached to the bottom surface of plate 53 and opens upwardly so as to encompass rotor assembly 30. Rotor assembly 30 is journaled to rotor drive assembly 50 by means of a vertical bearing or hub assembly 57 which extends between plates 51 and 52 and receives the rotor drive shaft 40.

The rotor drive assembly 50 is journaled to the machine frame for rotation along the same axis as rotor assembly 30 by means of a vertical drive shaft 60 which is attached to plate 53 in axial alignment with rotor drive shaft 40 by means of an end flange 61. Drive shaft 60 extends downwardly to a hub assembly 62, wherein a plurality of bearings 63 are provided for lateral and vertical support.

Figure 3:
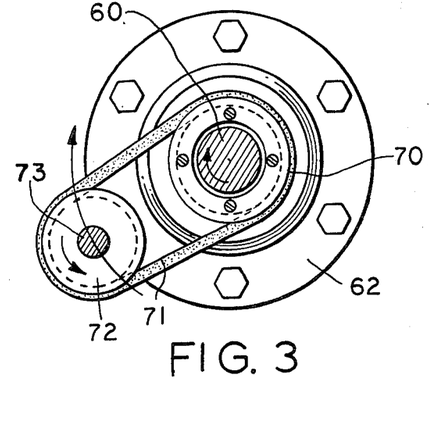
FIG. 3 is a cross-sectional view taken along line 3—3 of FIG. 2 showing the drive belt arrangement for the rotor drive assembly.
Figure 4:
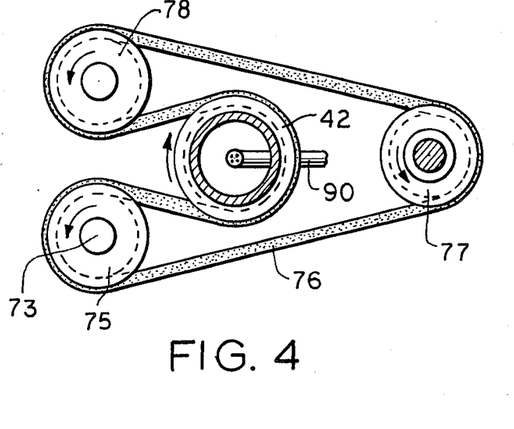
FIG. 4 is a cross-sectional view taken along line 4—4 of FIG. 2 showing a drive belt arrangement for the rotor assembly.

To provide drive power to the rotor drive assembly, the bottom end of drive shaft 60 is fitted with a drive pulley 64. This pulley is coupled by a drive belt 65 to a motor pulley 66, which is carried on the drive shaft 67 of a conventional drive motor 68. To provide drive power to rotor assembly 30, the top surface of hub assembly 62 is fitted with a stationary ring-type pulley 70. As shown most clearly in FIG. 3, this pulley is coupled by a belt 71 to a lower planetary drive pulley 72, which is fitted to the bottom end of a planetary drive shaft 73. Shaft 73 is journaled by means of a bearing assembly 74 to the bottom plate member 53 of rotor drive assembly 50. An upper planetary drive pulley 75 is fitted to the top end of shaft 73 and, as shown most clearly in FIG. 4, this pulley is coupled by a drive belt 76 to rotor drive pulley 42 with the assistance of first and second idler pulleys 77 and 78, journaled to plate members 52 and 53, respectively. Reference is made to the copending application of Mirza A. Khoja, et al., Ser. No. 620,991, filed Oct. 9, 1975, now U.S. Pat. No. 3,986,442 for a complete discussion of this drive belt arrangement.

By reason of the aforedescribed drive belt arrangements, rotor assembly 30 is caused to turn in the same direction as, and at twice the rotational speed of, rotor drive assembly 50. In the illustrated embodiment, as the rotor drive assembly 50 is turned clockwise (as viewed from above) by motor 68, planetary drive shaft 73 and upper planetary drive pulley 75 turn counterclockwise by reason of belt 71 and the stationary pulley 70. The counterclockwise rotation of pulley 75 results in clockwise rotation of rotor drive pulley 42, and hence of rotor assembly 30, by reason of the loop-back arrangement of belt 76 between these pulleys.

The necessary 2:1 speed relationship between rotor assembly 30 and rotor drive assembly 50 is maintained by the relative diameters of the drive pulleys. Specifically, the same ratio of diameters are maintained between pulley 70 and pulley 72 as between pulley 42 and pulley 75. This assures that the planetary drive arrangement will have a direct transfer ratio of 1:1 which, when the rotation of the planetary drive shaft 73 about the axis of rotation of drive assembly 50 is taken into account, results in an ultimate transfer ratio of 2:1. As will become evident presently, this relationship of relative speed and direction is necessary if the system is to operate without the use of rotating seals.

Figure 11:
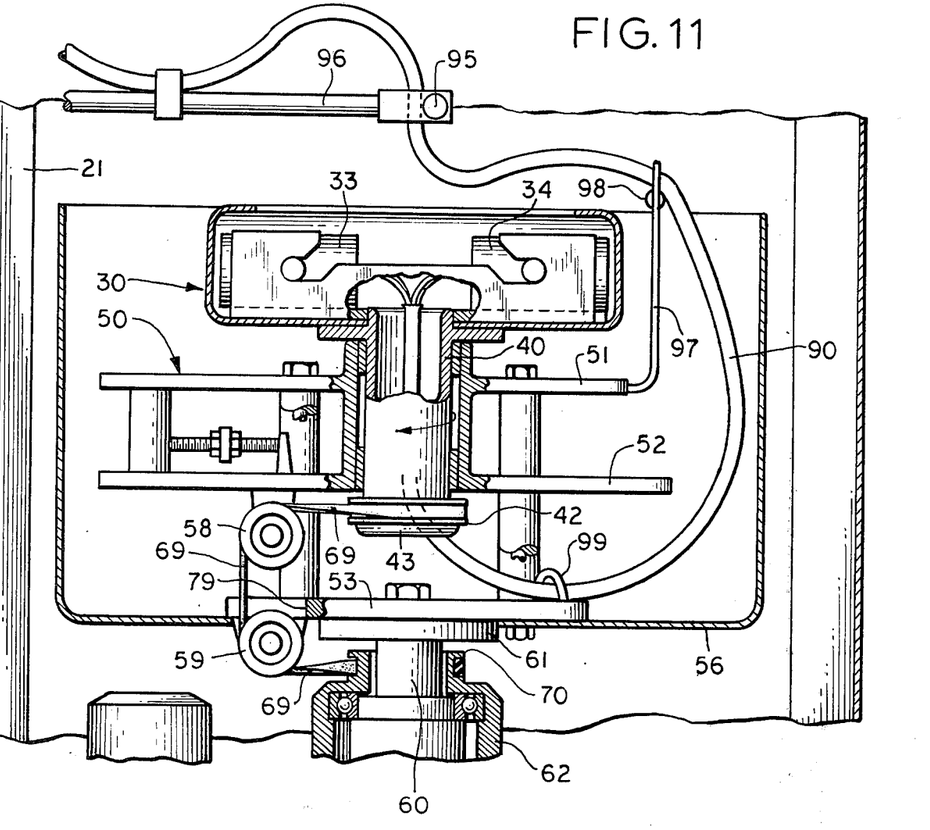
FIG. 11 is a front elevational view similar to FIG. 7 showing an alternate drive arrangement for the rotor assembly of the liquid processing apparatus.
Figure 12:
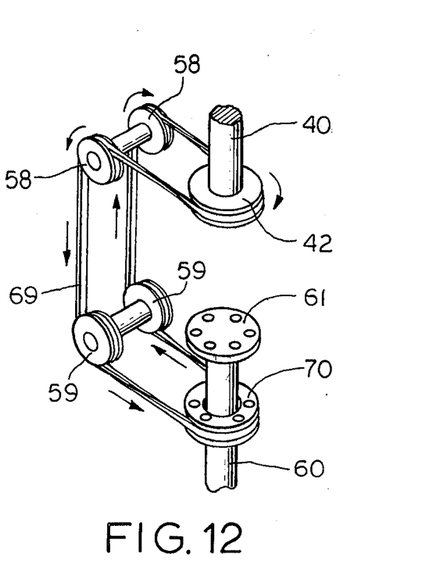
FIG. 12 is a diagrammatic illustration useful in understanding the operation of the alternate drive arrangement.

An alternate drive arrangement for rotor assembly 30 is shown in FIGS. 11 and 12. A first pair of laterally-spaced idler pulleys 58 is mounted on the bottom surface of plate member 52 and a second pair of similarly spaced idler pulleys 59 is mounted on the bottom surface of plate member 53. A drive belt 69 is routed over these pulleys from the stationary ring-type pulley 70 to the rotor drive pulley 42 as shown in FIG. 12. An aperture 79 is provided in plate member 53 to accommodate the belt.

In operation, as rotor drive assembly 50 is rotated clockwise by motor 68, drive belt 69 establishes a clockwise rotation of rotor assembly 30. Assuming that stationary pulley 70 and rotor drive pulley 42 have the same diameter, the rotational speed of rotor assembly 30 will be exactly twice that of rotor drive assembly 50, by reason of the combined effect of the direct 1:1 drive relationship established by pulleys 70 and 42 and the planetary motion of idler pulleys 58 and 59 about the rotational axis of rotor assembly 30.

The drive belts and pulleys utilized to drive the rotor and rotor drive assemblies may be conventional cogged belts and pulleys of the type commonly used for timing applications where slippage is to be avoided. Drive belts 65 and 71 have cogs on their inside surfaces only, whereas drive belt 76 has cogs on both its inside and outside surfaces.

Figures 5, 6:
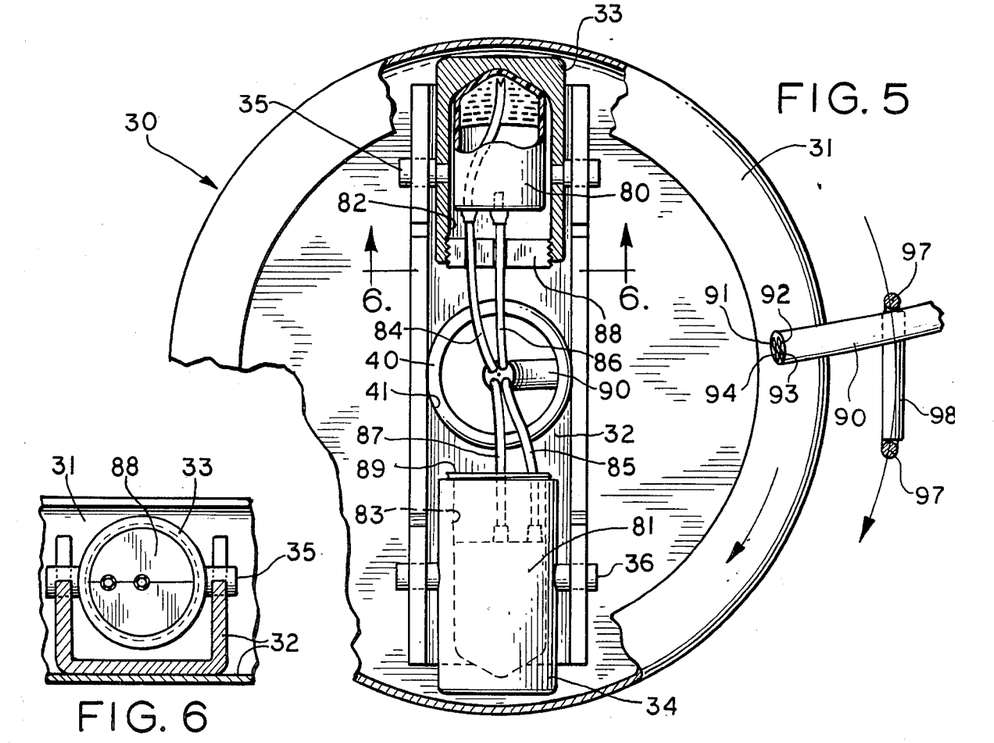
FIG. 5 is a top plan view of the cell processing apparatus partially broken away and partially in cross section showing cell wash bags in position for centrifugation.
FIG. 6 is a cross-sectional view taken along line 6—6 of FIG. 5 showing the covers of the support cups in which the cell wash bags are contained during centrifugation.

Referring to FIG. 5, the cell washing operation is performed in a pair of wash chambers taking the form of collapsible plastic wash bags 80 and 81. These wash bags, which preferably form part of a disposable pre-sterilized sealed flow system, the structure and operation of which is described in the co-pending application of the present inventor, Ser. No. 657,186 filed Feb. 11, 1976, a continuation-in-part of application Ser. No. 562,749, filed Mar. 27, 1975 and assigned to the present assignee, and which may be formed of a hemorepellent plastic material such as polyvinylchloride resin lined with a silicon rubber compound or other hemocompatible material, are preferably formed with a cylindrical body portion and a conical end portion. Complementarily formed cavities 82 and 83 are provided in cups 33 and 34 for receiving the wash bags.

Wash bags 80 and 81 have respective ones of inlet tubes 84 and 85 and outlet tubes 86 and 87 heat-sealed into communication with their interiors. The portions of the inlet tubes 84 and 85 which extend within the interiors of the bags are of sufficient length to extend to the apexes of the cone-shaped end portions of the bags when the bags are fully distended by centrifugal force. This is desirable for optimum washing action, since the cell mass congregates in the conical portions of the wash bags when under centrifugation. Outlet tubes 86 and 87 terminate in the walls of the wash bags. The overall length of the inlet and outlet tubes outside of the containers is not critical and need be only sufficient to provide for connection to the balance of the cell processing system.

The support cups 33 and 34 are preferably provided with removable covers 88 and 89 which prevent the wash bags from being dislodged during centrifugation. As shown in FIG. 6, these covers may be formed in two sections so that the inlet and outlet tubes can be passed through the covers when the wash bags in the cups.

Figures 8, 9:
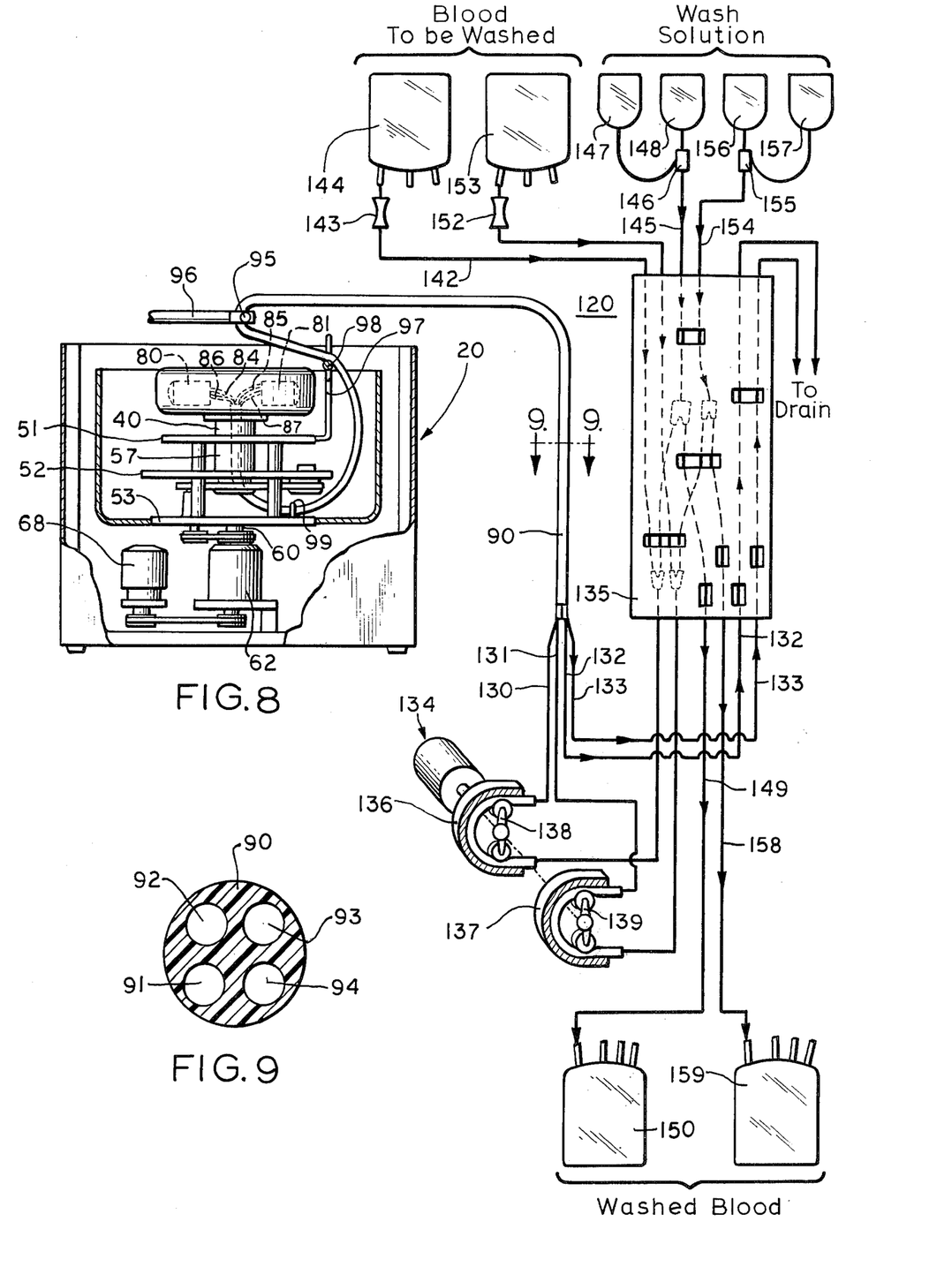
FIG. 8 is a flow diagram of a cell processing system constructed in accordance with the invention for reconstituting glycerolized red blood cells.
FIG. 9 is an enlarged cross-sectional view taken along line 9—9 of FIG. 8 showing the construction of the umbilical cord utilized in the cell processing system of FIG. 8.

Fluid communication is established between wash bags 80 and 81, which rotate with rotor assembly 30, and the non-rotating portion of the cell processing system, by means of an umbilical cable 90 containing four separate passageways or conduits 91–94 (FIGS. 5 and 9). Conduits 91–94, which may be formed by individual lengths of tubing joined together to form cable 90, or by passageways extruded into a single length of cable, are connected to respective ones of tubes 84–87. As best shown in FIGS. 1 and 2, umbilical cable 90 is suspended from a point above and axially aligned with rotor assembly 30 by means of a clamp 95 located at the end of a stationary support arm 96. From this point the cable extends generally downwardly and radially outwardly, passing through U-shaped guide means in the form of a pair of vertical guide rods 97 and a cross-connecting support roller 98 carried on plate member 51, then downwardly and radially inwardly through a support loop 99 carried on plate member 53, and then upwardly through the hollow center of rotor drive shaft 40 to a location between cups 33 and 34, where the umbilical cable connects with the inlet and the outlet tubes from wash bags 80 and 81. Fairing 43, which is journaled to drive shaft 40 at its bottom end so as to rotate freely with respect thereto, as shown in FIG. 10, serves to reduce friction between umbilical cable 90 and drive shaft 40.

The rotor drive assembly 50 is maintained in radial balance by means of an annular weight 100 carried on a radially-extending threaded support member 101 on plate member 52 opposite the umbilical guide rods 97. By turning weight 100 on member 101 the weight can be positioned to compensate for the weight of the opposite side of the rotor drive assembly, including the weight imposed by the umbilical cable 90 as it rests on support 98. A similar arrangement is provided on plate member 52 for achieving lateral balance. An annular weight 102 carried on a laterally-extending threaded support member 103 is provided for laterally balancing the drive plate assembly.

Umbilical cable 90 is prevented from becoming completely twisted during rotation of rotor assembly 30 by the coaxial half-speed rotation of rotor drive assembly 50, which imparts an orbit-like rotation with respect to the rotor axis to the umbilical cable through guide members 97 and 98. In this respect the present apparatus is similar to that described in U.S. Pat. No. 3,586,413, issued to Dale A. Adams on June 22, 1971. Since a complete explanation of the basic principle behind the present apparatus can be had by reference to that patent, it suffices to summarize here that if rotor assembly 30 is considered as having completed a first 360° rotation and rotor drive assembly 50 a 180° half-rotation in the same direction, the umbilical cable 90 will be subjected to a 180° twist in one direction about its axis. Continued rotation of rotor 30 for an additional 360° and drive assembly 50 for an additional 180° will result in umbilical cable 90 being twisted 180° in the other direction, returning the cable to its original untwisted condition. Thus, umbilical cable 90 is subjected to a continuous partial twist or flexure or bending during operation of the cell processing apparatus but is never completely rotated or twisted about its own axis.

While the centrifugal apparatus 20 has been shown in connection with the processing of biological cells, it will be appreciated that the apparatus has other applications, such as the centrifugal processing of chemicals or waste liquids, or applications wherein continuous energy communication must be maintained between a stationary terminal and a rotating terminal by means of an energy-transmitting channel which itself does not rotate about its own axis. For example, it would be possible to maintain optical communication by means of flexible fiber optics and electrical communication by means of flexible electrical conductors.

Figure 7:
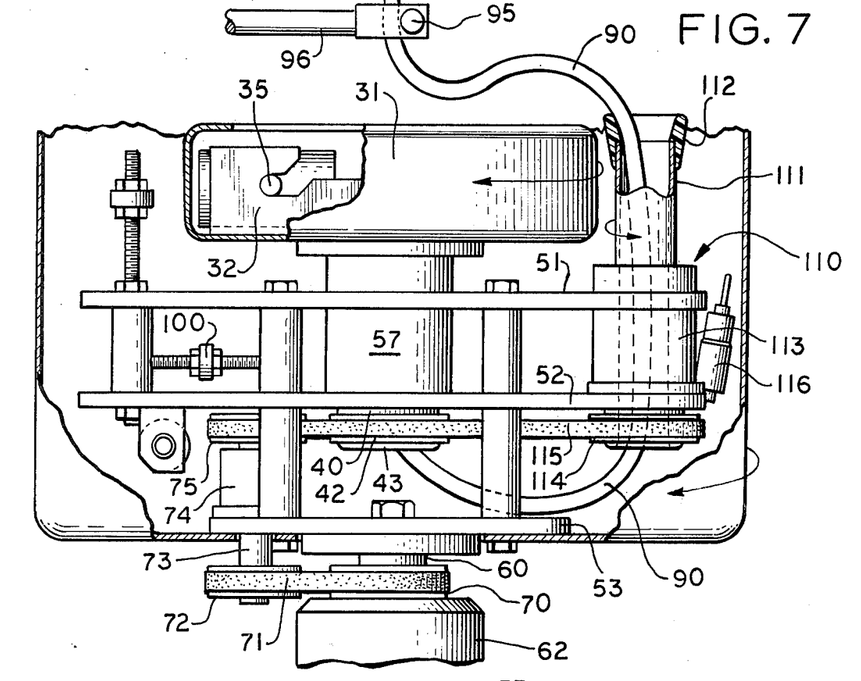
FIG. 7 is a front elevational view showing an alternate construction of the cell processing apparatus wherein a guide member having planetary motion is provided for the umbilical cable.

An alternate construction for the cell processing apparatus, wherein umbilical cable 90 is provided with a rotatably driven tubular guide assembly 110, is shown in FIG. 7. The guide assembly, which includes a hollow vertically-aligned tube 111 fitted with a fairing cap 112 at its top end, is journaled to plate members 51 and 52 by means of a bearing assembly 113. The bottom end of tube 111 is fitted with a pulley 114, which is coupled to the upper planetary drive pulley 75 by means of a belt 115 routed similarly to belt 76 in the four pulley belt arrangement shown in FIG. 4, with pulley 114 taking the place of pulley 77. The effect of this arrangement is that the umbilical guide tube 111 is rotated in the opposite direction to and at one-half the speed of rotor drive shaft 40, thus establishing a planetary-like relationship with respect to the rotor axis. That is, as rotor drive assembly 50 rotates, guide tube 111 may be thought of as always facing in the same direction with respect to a stationary observes. As a result, friction between the guide tube and umbilical cable 90 is minimized.

One problem encountered with incorporating the powered guide assembly 110 on the rotating rotor drive assembly 50 is maintaining adequate lubrication in bearing assembly 113. This problem has been overcome by means of a novel centrifugatably-powered lubrication system of which the present applicant is a co-inventor, which system is described and claimed in the copending application of Houshang Lolachi et al, Ser. No. 620,513, filed on Oct. 8. 1975.

The heretofore described cell processing apparatus 20 is shown in FIG. 8 incorporated in a processing system for washing red blood cells. The blood processing system includes, in addition, a pre-sterilized disposable flow system 120 capable of simultaneously processing two batches of glycerolized red blood cells without the use of rotating seals. The structure and operation of this flow system are covered in detail in the aforementioned application Ser. No. 657,186.

In the processing system illustrated in FIG. 8, fluid communication is established with wash bags 80 and 81, which comprise part of the disposable flow system 120, by means of passageways 91–94 in umbilical cable 90. These passageways are connected to respective ones of the inlet and outlet tubes 84–87 associated with wash bags 80 and 81 and serve to carry fluids to and from the bags. The umbilical cable 90, which is preferably formed as a single flexible extrusion of polyvinylchloride or similar material, extends from a central location on the rotor assembly 30 axially downwardly through the center of drive shaft 40, radially outwardly through guide member 99, and upwardly between guide members 97 to the centrally located clamping means 95 of the stationary arm 96.

Since flow system 120 is furnished as an integral pre-sterilized system, in installing the flow system in cell processing apparatus 20 all of the movable components of the system, i.e., wash bags 80 and 81, tubing segments 84–87, and the adjacent portion of umbilical cable 90 extending to clamp 92, are passed through guide members 97 and 99 and the axial passageway through drive shaft 40. In the case of the alternate construction for the guide member shown in FIG. 7, these components are also passed through the axial passageway of guide tube 111.

At the other end of umbilical cable 90 passageways 91–94 are connected to respective ones of four conventional transparent interconnecting tubes 130–133, which may be formed of polyvinylchloride or other suitable material. Tubes 130 and 131 are routed through a conventional two-section reversible roller pump 134 to a junction block 135 wherein communication is established between these tubes and supplies of glycerolized red blood cells or saline wash solution, or reservoirs for containing reconstituted blood. Roller pump 134, which may be entirely conventional in design and construction, includes a pair of arcuate mandrels 135 and 137 in which tubes 130 and 131 are seated, and a pair of rotating pressure roller assemblies 138 and 139 which bear against these tubes as they rotate so as to force liquids to flow through the tubes in a direction dependent on the direction of rotation of the assemblies.

Tube 130, which connects with passageway 91 in cable 90 and inlet tube 84 of wash bag 80, is connected by Y connectors within junction block 135 to a tube 142, which extends through a filter chamber 143 to a container 144 containing a first batch of glycerolized red blood cells to be processed, and to a tube 145, which extends through a tube clamp valve 146 to a pair of parallel-connected containers 147 and 148 containing saline wash solution for the first blood batch. Tube 130 is also connected in block 135 to a tube 149, which connects to a container 150 for receiving blood reconstituted from the first batch of glycerolized red blood cells. Similarly, tube 131 is connected by a tube 151 and a filter 152 to a container 153 containing a second batch of glycerolized red blood cells to be processed, by a tube 154 and a tube clamp valve 155 to a pair of parallel-connected containers 156 and 157 containing wash solution for the second blood batch, and by a tube segment 158 to a container 159 in which blood reconstituted from the second batch of glycerolized red blood cells is received.

In operation, the two batches of glycerolized red blood cells to be processed are pumped from containers 144 and 153 by roller pump 134 into wash bags 80 and 81 through tubes 130 and 131, umbilical passageways 121 and 122, and inlet tubes 84 and 85, respectively. By reason of the centrifugal force exerted by rotor assembly 30, which may rotate at speeds in excess of 2000 RPM, the red blood cells congregate at the apex of the conical portion of the extended wash bags. Saline wash solution is now pumped from container pairs 147, 148 and 156, 157 by roller pump 134 through the same flow path. The saline wash solution flows through the centrifugally-congregated red cell mass, the spent solution flowing out through outlet tubes 86 and 87, umbilical passageways 123 and 124, and tubes 132 and 133 as waste.

This continues until the entire supply of wash solution has been used, the glycerol preservative in the red blood cells being replaced by the saline solution to form reconstituted blood. The reconstituted blood is now pumped from wash bags 80 and 81 through inlet tubes 84 and 86, umbilical passageways 121 and 122, tubes 130 and 131, and tubes 149 and 158 to containers 150 and 159, respectively. Pump 134 is operated in reverse during this operation.

While the illustrated embodiments show two processing chambers or wash bags and an umbilical cable having four passageways for similtaneously processing two batches of cells, it will be appreciated that a greater or lesser number of chambers or wash bags and passageways could be provided to permit simultaneous processing of a lesser or greater number of batches, the only limitation being the amount of available space on the rotor assembly and the practicality of forming the umbilical cable with the required number of passageways. Furthermore, while the rotor and rotor drive assemblies have been as powered by drive belts, it would also be possible to use gear arrangements to achieve the same results.

Figure 13:
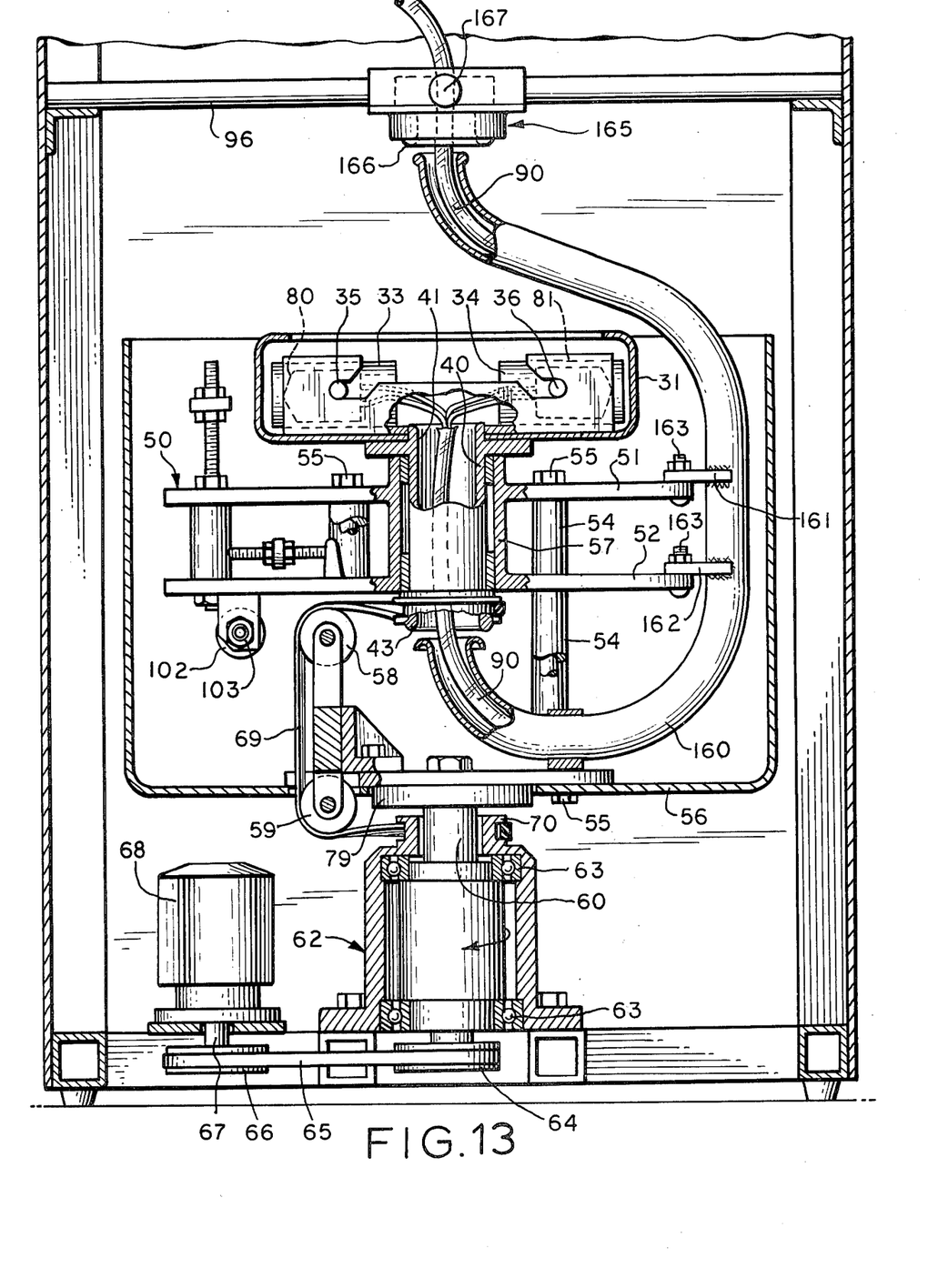
FIG. 13 is a front elevational view similar to FIG. 11 wherein an enclosed guide sleeve is provided to facilitate installing a flow system in the apparatus.

To provide for more convenient installation of the umbilical cable and to provide support for the cable during operation of the apparatus a guide sleeve 160 may be provided between the support arm 96 and fairing 43, as shown in FIG. 13. This sleeve, which is preferably formed of stainless steel or a similar high strength material, is preferably circular in cross section and substantially larger in diameter than the umbilical cable 90 to enable the cable and wash bags of the flow system to be threaded into position. A novel leader assembly for assisting the user in this threading operation is described and claimed in a co-pending application of the present applicant, Ser. No. 657,186, filed Feb. 11, 1976, and assigned to the present assignee.

The guide sleeve 160 is secured to the rotor drive assembly 50 by means of a pair of brackets 161 and 162 welded or otherwise attached to the outside surface of the sleeve wall. These brackets are attached to the top and bottom plates 51 and 52, respectively, of the rotor drive assembly by means of machine screws 163 or other appropriate fastening means so as to support the sleeve with its bottom end adjacent fairing 43 and its top end adjacent support arm 96. A support hub 165 having a free-rotating fairing 166 and a retaining clamp 167 is preferably provided on arm 96 near the upper end of the guide sleeve to anchor the umbilical cable to the stationary frame of the machine.

In operation, the guide sleeve rotates with the rotor drive assembly and the cable alternately twists 180° to the left and right within the sleeve, thereby maintaining fluid communication with the wash bags without the cable becoming completely twisted.

Figure 14:
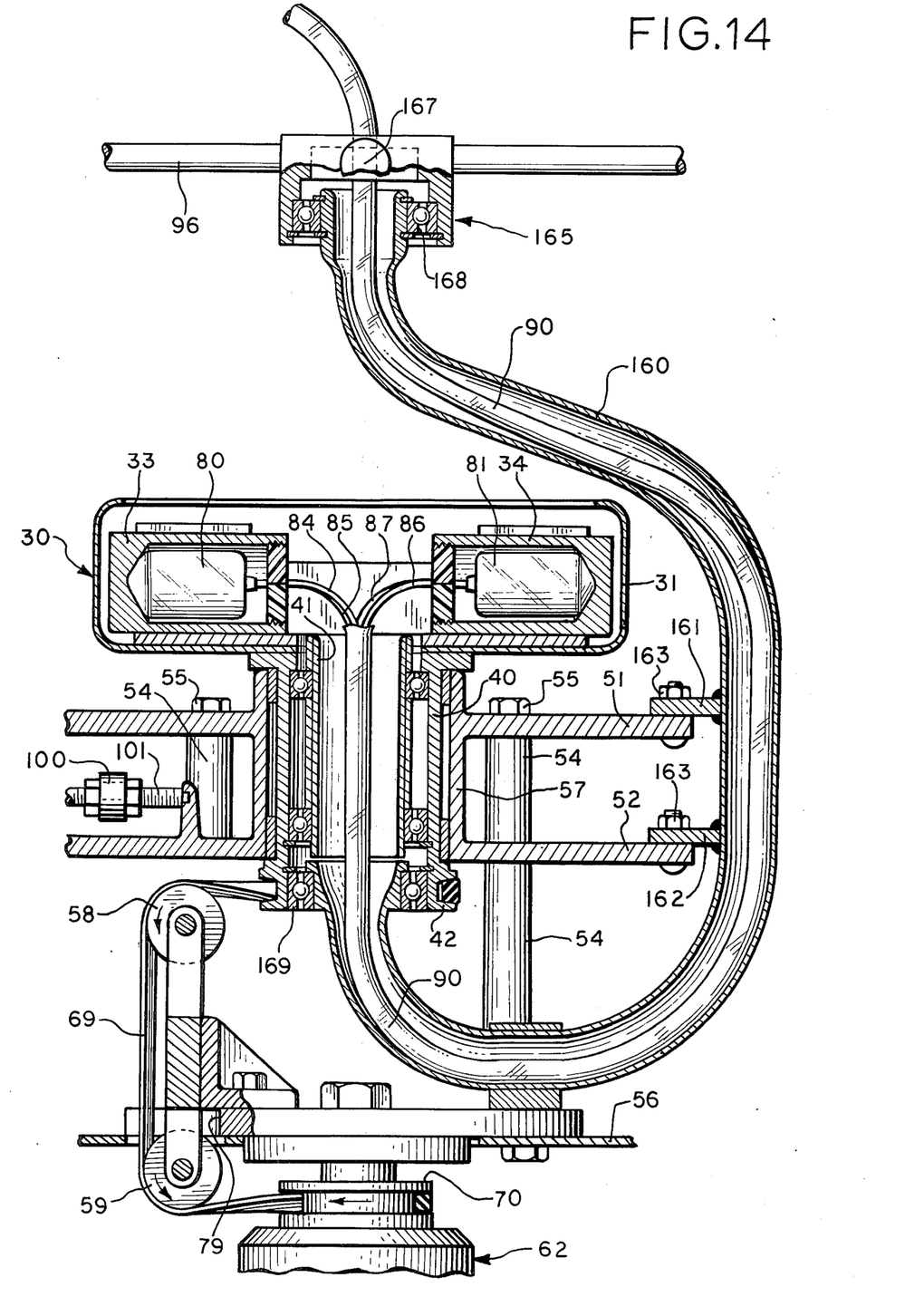
FIG. 14 is a front elevational view similar to FIG. 13 showing an alternate construction for the guide sleeve.

An alternate construction for the guide sleeve is shown in FIG. 14. In this embodiment the upper end of the guide sleeve 160 is journaled to the support hub 165 by means of a bearing assembly 168, and the bottom end of the sleeve is journaled to the bottom end of the rotor drive shaft 40 by means of a bearing assembly 169. This arrangement has the advantage of providing additional support to the guide sleeve and eliminates gaps between the ends of the sleeve and the rotor drive shaft and support hub.

Figure 15:
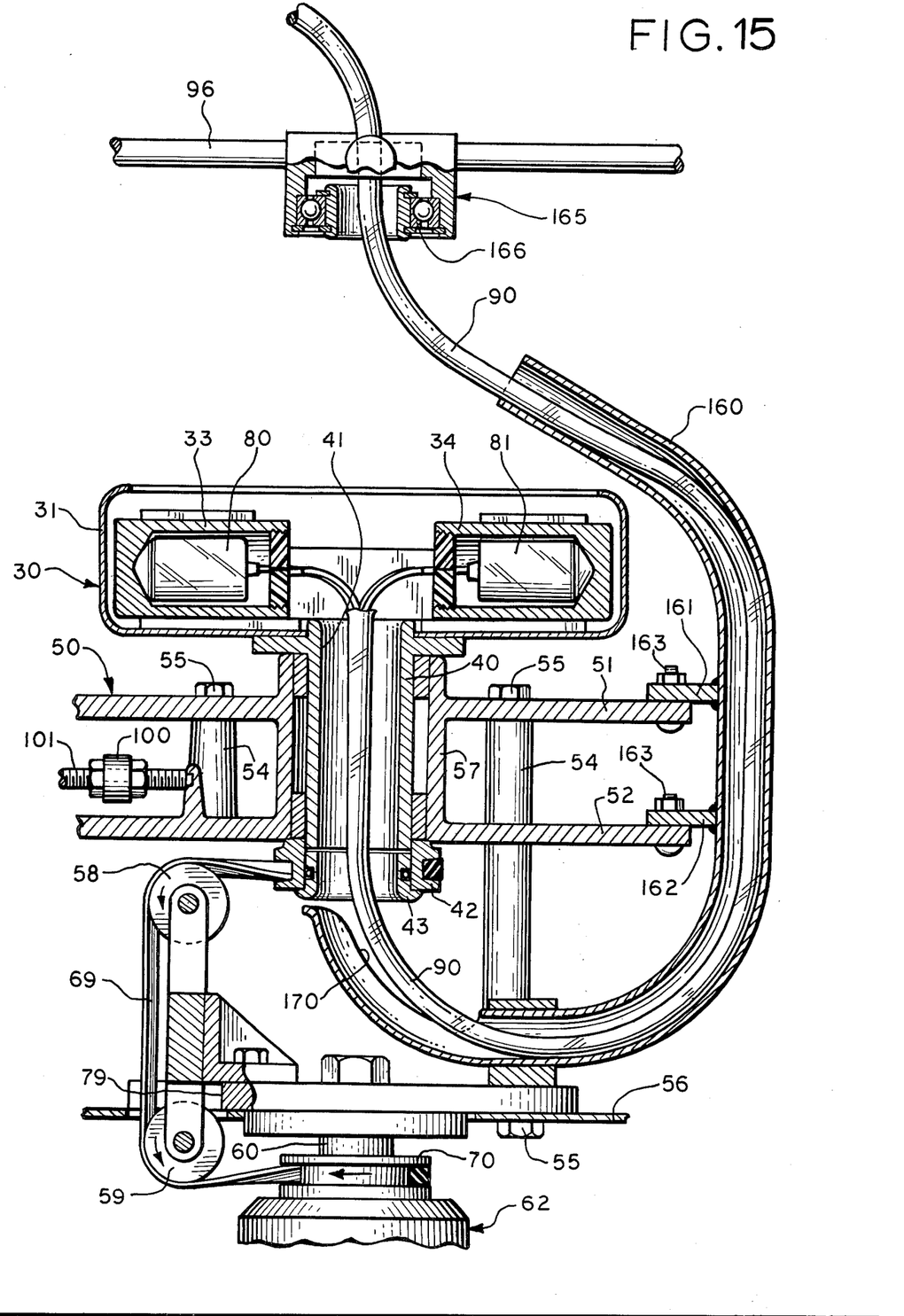
FIG. 15 is a front elevational view similar to FIG. 13 showing another alternate construction for the guide sleeve.

Another alternate construction for guide sleeve 160 is shown in FIG. 15. In this embodiment, which is similar to that shown in FIG. 13, the sleeve is shortened at its upper end so as to allow the umbilical cable to be unsupported as it extends from support hub 165 to the sleeve. At the bottom end of the sleeve a portion of the sleeve wall is cut away to form an open trough portion 170 in which the umbilical cable 90 lays prior to extending up into the center of the hollow rotor drive shaft 40. This arrangement, like that shown in FIG. 13, has the advantage of obviating the need for the guide sleeve to have a precise shape to interface with bearings at the support hub and rotor drive shaft. A further advantage of this arrangement is that access can be more readily obtained to the inside of the support sleeve than with the closed sleeve arrangements of FIGS. 13 and 14, thereby facilitating cleaning of the sleeve and threading of the flow system.

It will be appreciated that other constructions and shapes may be employed for the guide sleeve. For example, the sleeve may have a greater or lesser diameter to accommodate various sizes and constructions of the umbilical cable, and may be mounted to the rotor drive assembly by means other than mounting brackets, such as by clamps around the sleeve. Furthermore, a second sleeve or similarily shaped element (not shown) may be mounted on the rotor drive assembly in diametrically opposed relationship to sleeve 160 to balance the drive assembly, both dynamically and aerodynamically. In this case the sleeves may be mounted at right angles with respect to the rotor drive belt 69 and associated idler pullesy 58 and 59.

While the apparatus of the invention has been shown in conjunction with a red blood cell washing application, it will be appreciated that the apparatus has a wide range of other uses. For example, in the field of blood processing the apparatus may be used in plasmapheresis, erythropheresis, leukapheresis, and plateletpheresis, in either an inverto or an in-viro application. In such alternate uses a fluid flow system appropriate for the process is installed in the apparatus in a manner similar to the red blood cell processing flow system shown in FIG. 8.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. Apparatus for use in conjunction with a flexible communication conduit for maintaining communication with terminal means under centrifugation, comprising, in combination:
   a stationary base;
   a rotor drive assembly rotatably mounted to said base for rotation along a predetermined axis;
   a rotor assembly, including terminal means, said rotor assembly being rotatably mounted to said rotor drive assembly for rotation with respect thereto along said axis by means including a support shaft journaled to said drive assembly, said support shaft including a central axially-extending aperture;
   a rotor drive pulley locked for rotation with said rotor assembly;
   support means for supporting said communication conduit above said rotor assembly along said axis;
   guide means including a guide member on said rotor drive assembly for guiding the communication conduit from said support means through said axially-extending aperture to said terminal means, said guide means rotatably coupling said conduit to said rotor drive assembly with respect to said axis;
   said rotor drive assembly being rotatably mounted to said base by means of a support shaft axially-aligned with said axis of rotation;
   drive means for rotating said rotor assembly and said rotor drive assembly in like directions with a speed ratio of 2:1 to maintain communication without completely twisting said conduit, said drive means including a stationary pulley carried by said base, planetary drive means carried on said rotor drive assembly and coupled to said stationary pulley and said rotor drive pulley for driving said rotor assembly, said planetary drive means including a drive belt operatively engaged at one end to said stationary pulley and at its other end to said rotor drive pulley, and belt guide means comprising a pair of guide pulleys rotatably mounted on said rotor drive assembly for causing said drive belt to orbit with said rotor drive assembly about said predetermined axis of rotation.

2. Apparatus as defined in claim 1 wherein said belt guide means comprise at least a pair of guide pulleys having axis of rotation lying in a plane perpendicular to said predetermined axis.

3. Apparatus as defined in claim 2 wherein said belt guide means comprise first and second pairs of guide pulleys, said first pair of guide pulleys having axis of rotation lying in a first plane perpendicular to said predetermined axis, and said second pair of guide pulleys having axis of rotation lying in a second plane perpendicular to said predetermined axis; and
   wherein said first and second planes intersect said predetermined axis at spaced locations whereby the ends of said drive belt are aligned with said stationary and rotor drive pulleys.

4. Apparatus as defined in claim 3 wherein said stationary base pulley and said rotor drive pulley are of equal predetermined diameter, and said first and second pairs of guide pulleys each have a common axis of rotation and a spacing corresponding to said predetermined diameter.

5. Apparatus for use in conjunction with a flexible communication conduit for maintaining communication with terminal means under centrifugation, comprising, in combination:
   a stationary base assembly including bearing means defining a predetermined axis of rotation, and a stationaey drive pulley disposed along said axis;
   a rotor drive assembly rotatably mounted to said base by means of an axially aligned support shaft coacting with said bearing means for rotation along said predetermined axis;
   a rotor assembly, including terminal means on one side thereof, said rotor assembly being rotatably mounted to said rotor drive assembly for rotation with respect thereto along said axis by means including a support shaft journaled to said rotor drive assembly, said support shaft extending from the opposite side of said rotor assembly and including a central axially-extending aperture and a rotor drive pulley rotatably locked to said support shaft for rotation with said pulley;
   support means for supporting said communication conduit above said one side of said rotor assembly along said axis;
   guide means including a guide member on said rotor drive assembly for guiding the conduit from said support means through said axially-extending aperture to said terminal, said guide means rotatably coupling said conduit to said rotor drive assembly with respect to said axis; and
   drive means for rotatably driving said rotor drive assembly with respect to said base;
   said drive means including a drive belt operatively engaged at one end to said stationary drive pulley and at its other end to said rotor drive pulley, and belt guide means comprising a pair of guide pulleys rotatably mounted on said rotor drive assembly for causing said drive belt to rotate with said rotor drive assembly about said predetermined axis of rotation, for rotating said rotor assembly in the direction of said rotor drive assembly with a speed ratio of 2:1.

6. Apparatus as defined in claim 5 wherein said belt guide means comprise at least a pair of guide pulleys having axis of rotation lying in a plane perpendicular to said predetermined axis.

7. Apparatus as defined in claim 6 wherein said belt guide means comprise first and second pairs of guide pulleys, said first pair of guide pulleys having axis of rotation lying in a first plane perpendicular to said predetermined axis, and said second pair of guide pulleys having axis of rotation lying in a second plane perpendicular to said predetermined axis; and wherein said first and second planes intersect said predetermined axis at spaced locations whereby the ends of said drive belt are aligned with said stationary and rotor drive pulleys.

8. Apparatus as defined in claim 7 wherein said stationary base pulley and said rotor drive pulley are of equal predetermined diameter, and said first and second pairs of guide pulleys each have a common axis of rotation and a spacing corresponding to said predetermined diameter.

* * * * *